United States Patent [19]

Klein

[11] Patent Number: 4,710,947

[45] Date of Patent: Dec. 1, 1987

[54] COLLIMATOR FOR A RADIATION DIAGNOSTICS APPARATUS

[75] Inventor: Sigismund Klein, Nuremberg, Fed. Rep. of Germany

[73] Assignee: Siemens Aktiengesellschaft, Berlin and Munich, Fed. Rep. of Germany

[21] Appl. No.: 890,112

[22] Filed: Jul. 28, 1986

[30] Foreign Application Priority Data

Sep. 30, 1985 [DE] Fed. Rep. of Germany ....... 3534893

[51] Int. Cl.$^4$ .............................................. G21K 1/02
[52] U.S. Cl. ..................................... 378/147; 378/145; 250/505.1; 211/41; 248/231.2; 248/316.2
[58] Field of Search ................. 378/19, 145, 147, 149, 378/156, 204, 210; 250/505.1, 363 SH; 211/41; 248/231.2, 316.2

[56] References Cited

U.S. PATENT DOCUMENTS

| | | | |
|---|---|---|---|
| 2,986,281 | 5/1961 | Jordan | 211/41 |
| 3,566,175 | 2/1971 | Baldwin | 315/382 |
| 4,292,525 | 9/1981 | Tschunt | 378/149 |
| 4,414,473 | 11/1983 | Hoffman | 378/19 |
| 4,493,098 | 1/1985 | Riihimäki | 378/145 |

FOREIGN PATENT DOCUMENTS 2260014  8/1975  France .
0137656 10/1980  Japan ................................... 378/19

Primary Examiner—Craig E. Church
Assistant Examiner—John C. Freeman
Attorney, Agent, or Firm—Hill, Van Santen, Steadman & Simpson

[57] ABSTRACT

A collimator for a radiation diagnostics apparatus has two parallel spaced carriers each having a slot therein directed toward the radiation focus in which a collimator plate consisting of radiation absorbing material is inserted. The collimator plate is a sheet having at least one resilient tongue cut therein at each edge thereof which is received in the respective slots. The tongues are bent so as to project beyond the thickness of the plate and thus are disposed against an inside surface of the slots and thereby press the collimator plate against opposite respective surfaces of the slots.

3 Claims, 3 Drawing Figures

COLLIMATOR FOR A RADIATION DIAGNOSTICS APPARATUS

BACKGROUND OF THE INVENTION

1. Field of the Invention

The present invention relates to collimators for radiation diagnostics devices, and in particular to such a collimator having two spaced parallel carriers with one or more collimator plates of radiation-absorbing material inserted between the carriers in slots.

2. Description of the Prior Art

A radiation diagnostics installation as described in German Pat. No. 28 40 965 which permits slice images of an examination subject to be produced by absorption of x-radiation. Several hundred individual detector elements are provided for quantitatively documenting the x-radiation which penetrates the examination subject. The individual detector elements are attached to collimator plates which are held in position in respective slots in two spaced parallel carrier plates. The slots are directed toward the radiation focus.

In this embodiment, it is possible that the collimator plates may not be adequately fixed in the desired position because of the slots, due to manufacturing tolerances, may have a greater width than the thickness of a collimator plate. The collimator plates may thus have so much play within the slots that the plates are no longer aligned to the radiation focus. Shadowing and a reduced exploitation of the effective detector surface result.

SUMMARY OF THE INVENTION

It is an object of the present invention to provide a collimator for an X-ray diagnostics installation, wherein the collimator plate is held between two spaced parallel carriers in slots therein, and wherein the collimator plate remains properly oriented within the slots. It is a further object of the present invention to provide such a collimator which is relatively insensitive to manufacturing tolerances.

The above object is achieved in accordance with the principles of the present invention in a collimator wherein the collimator plates each consist of resilient sheet material having tongues cut at the respective edges thereof which are received in the slots, with the tongues being bent so as to project beyond the thickness of the collimator sheet.

The resilient tongues, when the plates are disposed in the carrier slots, are supported against one inside surface of the slots and press the collimator sheets against an opposite inside surface of the slots, so that the sheets are held without play within the slots. The slots in the carriers can be sawn or milled with less exacting tolerances, thereby simplifying the manufacturing process.

DESCRIPTION OF THE PREFERRED EMBODIMENTS

Figure 1:
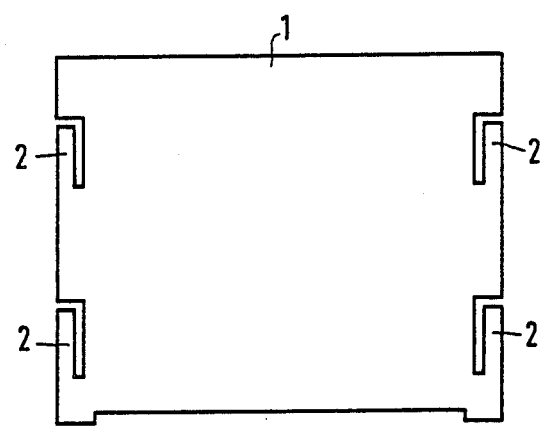
FIG. 1 is a plan view of a collimator plate constructed in accordance with the principles of the present invention.
Figure 2:
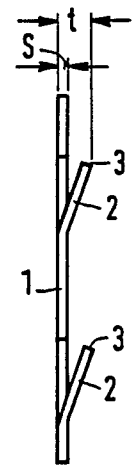
FIG. 2 is a side view of the collimator plate shown in FIG. 1.

A collimator plate 1 constructed in accordance with the principles of the present invention is shown in plan view in FIG. 1. The collimator plate 1 consist of resilient radiation-absorbing material, such as metal, and has at least one tongue 2 disposed at each edge thereof which is to be received in a carrier slot in the collimator. In the embodiment shown in FIG. 1, opposite edges of the collimator plate 1 each have two such tongues 2 therein. The tongues 2 may be produced by sawing or milling the lateral edges of the plate 1. As shown in FIG. 2, the metal tongues 2 are then bent out of the plan of collimator plate 1. The collimator plate may have a thickness S, however, the effective thickness caused by bending the tongues 2, measured to the free end 3 of the tongues, may be t.

Figure 3:
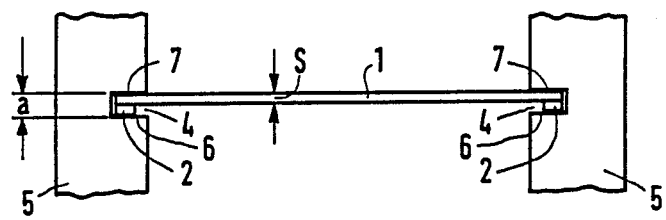
FIG. 3 is an end view of a collimator plate constructed in accordance with the principles of the present invention disposed in two spaced carriers.

A collimator plate 1 inserted in two slots 4 of spaced parallel carriers 5 is shown in FIG. 3. The slots 4 have a width "a" which is selected of a maximum size but which does not exceed the effective width T of the collimator plate 1. The tongues 2 are thereby compressed when the collimator plate 1 is inserted in the slots 4. The tongues 2 are disposed against an inside surface 6 of the slot 4 and press the collimator plate 1 against the opposite inside surface 7. The collimator plate 1 is thereby held without play in the slots 4.

An additional advantage of this embodiment is improved ease of interchangeability of the collimator plates. If the plates were glued into the slots, for example, the precision of the focussing would be limited by the plate and slot tolerances. Using the collimator plates described herein, the slots can have a greater width "a" and a greater tolerance can thus be accepted.

Although modifications and changes may be suggested by those skilled in the art it is the intention of the inventor to embody within the patent warranted hereon all changes and modifications as reasonably and properly come within the scope of his contribution to the art.

I claim as my invention:

1. An X-ray collimator comprising an X-ray opaque collimator plate and spaced parallel carriers, said carriers having slots to receive said plate; said collimator plate having resilient tongues at respective edges thereof which are received in said slots, said tongues projecting beyond a thickness of a collimator plate and when received in said slots said tongues pressing against an inside surface of the respective slots and pressing the collimator plates against another inside surface of said slots opposite thereto.

2. A collimator as claimed in claim 1, wherein at least said tongues consist of resilient sheet metal.

3. A collimator as claimed in claim 1, wherein said collimator plate is planar, and wherein said collimator tongues project from said collimator plate such that said collimator plate has an effective thickness which is greater than a thickness of said slots.

* * * * *